United States Patent [19]

Liautaud

[11] Patent Number: 4,815,838

[45] Date of Patent: Mar. 28, 1989

[54] VISOR MOUNTED LENS

[76] Inventor: John R. Liautaud, 180 Stonegate, Cary, Ill. 60013

[21] Appl. No.: 154,919

[22] Filed: Feb. 11, 1988

[51] Int. Cl.⁴ .......................... G02C 7/10; G02C 7/16
[52] U.S. Cl. ..................................... 351/158; 351/44; 351/45; 2/12
[58] Field of Search ....................... 351/41, 44, 45, 46, 351/47, 48, 49, 158; 2/12

[56] References Cited

U.S. PATENT DOCUMENTS 2,638,593 4/1951 Eloranta .................................. 2/12

Primary Examiner—Rodney B. Bovernick
Attorney, Agent, or Firm—Fitch, Even, Tabin & Flannery

[57] ABSTRACT

Protective apparatus for shielding the eyes against the entrance of foreign matter. The apparatus includes a one-piece molded plastic visor which is formed of resilient material and includes a brim having an inner surface for engaging the forehead. The visor further includes a bill extending outwardly with the visor having first and second spaced legs extending rearwardly from the brim for compressively holding the head therebetween. The legs and the brim form a spring system which permits resilient deflection of the legs. The protective apparatus further includes a transparent shield dependent from the brim for overlaying the eyes. The shield includes a first end positioned adjacent the first leg and a second end disposed adjacent the second leg with an upper surface extending intermediate the ends and positioned closely adjacent the bill. The apparatus additionally includes a connection for fixably holding the shield to the brim. This connection is located inwardly of the shield ends to permit relative movement between the shield ends and adjacent portions of the brim when the legs are deflected thereby permitting mounting of the apparatus on the head.

7 Claims, 2 Drawing Sheets

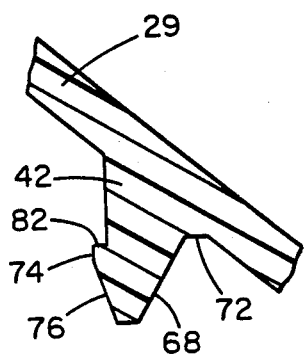 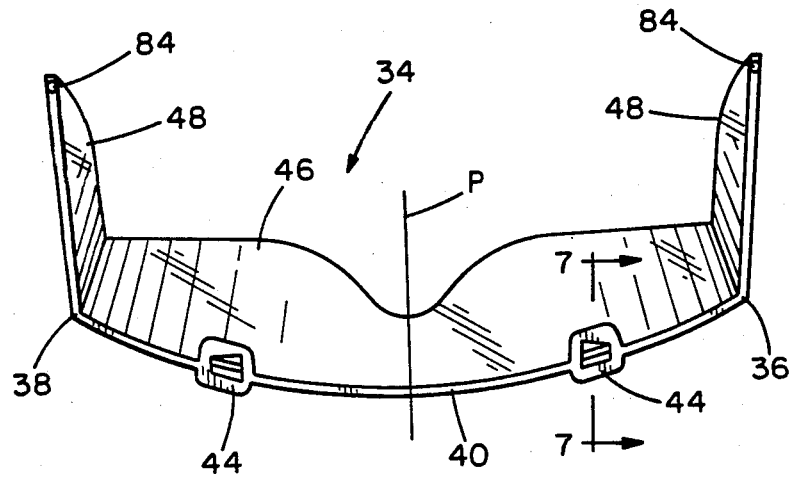 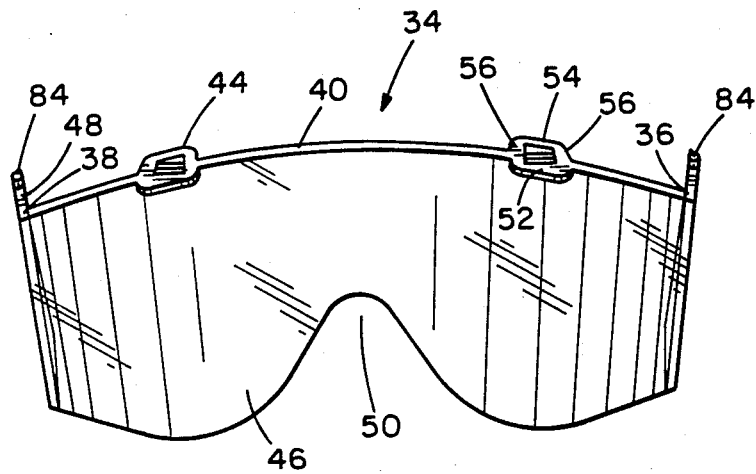 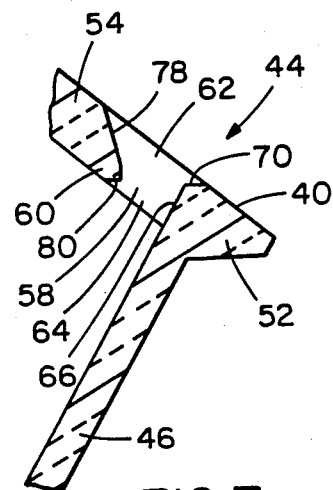 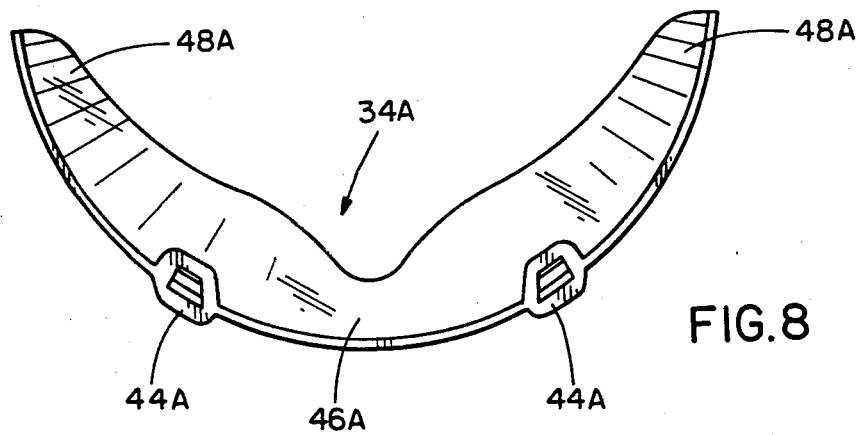

VISOR MOUNTED LENS

The present invention relates ro protective apparatus and, more specifically, to a lens to protect the eyes of the wearer, for example, against foreign material and/or harmful radiation.

BACKGROUND OF THE INVENTION

Safety considerations mandate that a visitor in, for example, industrial locations and at construction sites use protective eyewear to guard the eyes against foreign matter. Safety glasses, while effective, are relatively expensive and can be cumbersome to put on. Additionally, if the visitor wears prescription glasses, his inability to see well with non-prescription safety glasses might persuade that person to forego the additional protection afforded by the safety glasses.

It is also common for hard hats to carry a bulbous viewing shield. These hard hats are expensive, relatively heavy and can be uncomfortable to wear in warm weather and in high humidity because air circulation about the head is greatly limited. Of course, low cost, ease of donning, and comfort are factors which operate in favor of increased use of protective eyewear.

Various hats have been proposed having eyeglass components which are pivotally attached to the brim so that they can be pivoted from a storage position adjacent the bill to a use location in front of the eyes. For further information concerning the operation and structure of such hats, reference may be made to U.S. Pat. Nos. 4,541.125; 3,383,155; 2,691,164; 1,833,741; 1,514,111; 1,334,878; 1,282,723; 862,795 and 256,393. It is also known to manufacture a visor by molding a thermoplastic material. Such visors include a brim with a pair of resilient head engaging legs extending rearwardly from the brim to hold the head of the wearer. Such visors are used to reduce glare at, for example, a sporting event.

SUMMARY OF THE INVENTION

Among the several aspects and features of the present invention may be noted the provision of improved protective eyewear. The protective eyewear is easy to put on as it simply requires deflecting two head engaging resilient legs and moving the eyewear rearwardly until the brim bears upon the forehead. The eyewear permits free circulation of air about the top of the head and further permits the user to continue to wear his or her prescription glasses. The eyewear permits installation of different styles of transparent shields on a common visor. Furthermore, the eyewear is comfortable to wear as it does not require the ears or the nose to support substantial weight of the eyewear. Additionally, the protective eyewear of the present invention is reliable in use, has long service life and is relatively easy and inexpensive to manufacture. Other aspects and features of the present invention will be, in part, apparent and, in part, pointed out hereinafter in the following specification and in the accompanying drawings.

Briefly, the protective eyewear apparatus of the present invention includes a one-piece molded plastic visor which is formed of resilient material and includes a brim having an inner surface for engaging the forehead and a bill extending outwardly. The visor further includes first and second spaced legs extending rearwardly from the brim for compressively engaging the head. The legs and brim cooperate to form a spring system allowing resilient deflection of the legs from an as-formed position to an extended position thereby permitting placement of the visor on the head by moving the visor rearwardly until the brim inner surface engages the forehead. A one-piece transparent shield is dependent from the brim for overlaying the eyes. The shield includes a first end disposed adjacent the first leg, a second end disposed adjacent the second leg and an upper surface extending intermediate the ends and positioned closely adjacent the bill. The protective apparatus further includes a pair of spaced posts extending from the bill with the shield having a pair of sockets for receiving the posts. The connection of the shield to the bill does not result in substantial stiffening of the spring system so as to unduly interfere with the ease with which the legs can be deflected. The visor may be lined with a sweatband. Also an elastic band can be provided attached to the free end of the legs to permit the visor to hang from the user's neck when the user is not wearing the apparatus to protect the eyes.

BRIEF DESCRIPTION OF THE DRAWINGS

FIG. 4 is an enlarged detail illustrating a lens-mounting bayonet-type attachment carried by the visor;

FIG. 5 is a plan view of the shield of FIG. 1 illustrating sockets integral with the shield for receiving the attachments;

FIG. 6 is a front elevational view of the shield;

FIG. 7 is a partial sectional view taken generally along line 7—7 of FIG. 5; and FIG. 8 is a plan view of an alternative embodiment of the shield of the present invention.

Corresponding reference characters indicate corresponding components throughout the several views of the drawings

DESCRIPTION OF THE PREFERRED EMBODIMENT

Figure 1:
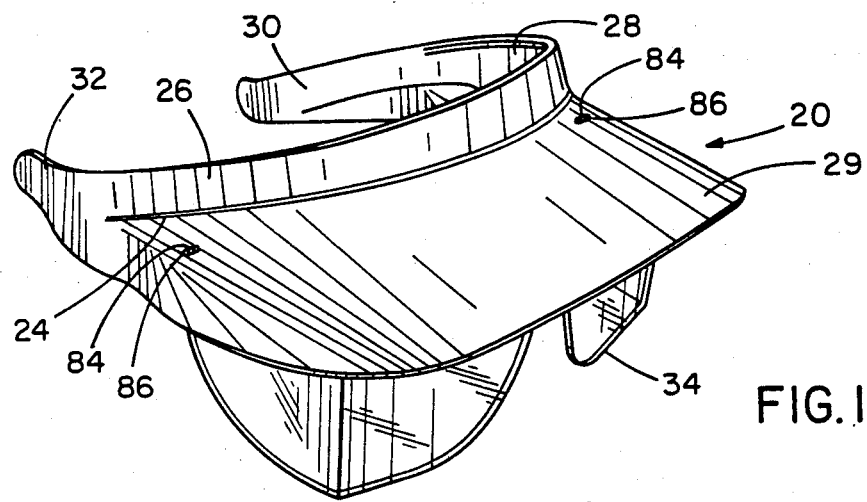
FIG. 1 is a perspective view of a visor mounted viewing shield embodying various aspects of the subject invention.

Referring now the drawings, protective apparatus or eyewear embodying various aspects of the present invention is generally indicated in FIG. 1 by reference numeral 20. The eyewear functions to protect the wearer's eyes from the entrance of foreign matter, from splashes and/or from radiation. The eyewear 20 includes a visor 22, best shown in FIGS. 2 and 3, having a brim 24 including an annular wall 26 with an inner surface 28 for bearing on the forehead of the wearer. A bill 29 extends outwardly from wall 26. A first leg 30 and a second leg 32, spaced from leg 30, extend rearwardly from the brim for compressively engaging the head of the wearer. A transparent shield 34 depends from the bill 29, and includes a first end 36 disposed adjacent the first leg 30 and a second end 38 positioned adjacent the second leg 32. The shield 34, which is best shown in FIGS. 5 and 6, also has an upper surface 40 extending between the ends 36, 38 and which is positioned, when the visor and shield are held together, closely adjacent the bottom of the bill 29.

The eyewear 20 also includes means fixedly connecting the shield 34 to the bill. This means preferably takes the form of a pair of bayonet-like posts 42 having enlarged heads, best shown in FIG. 4, which extend downwardly from the bill. A pair of sockets 44, aligned with corresponding posts 42, are formed at the top of the shield for receiving the posts in an interference fit. The sockets 44 are disposed inwardly of the ends 36, 38 of the shield so that the attachment of the shield to the visor does not substantially stiffen the visor so as to make it difficult for the wearer to don.

Figure 2:
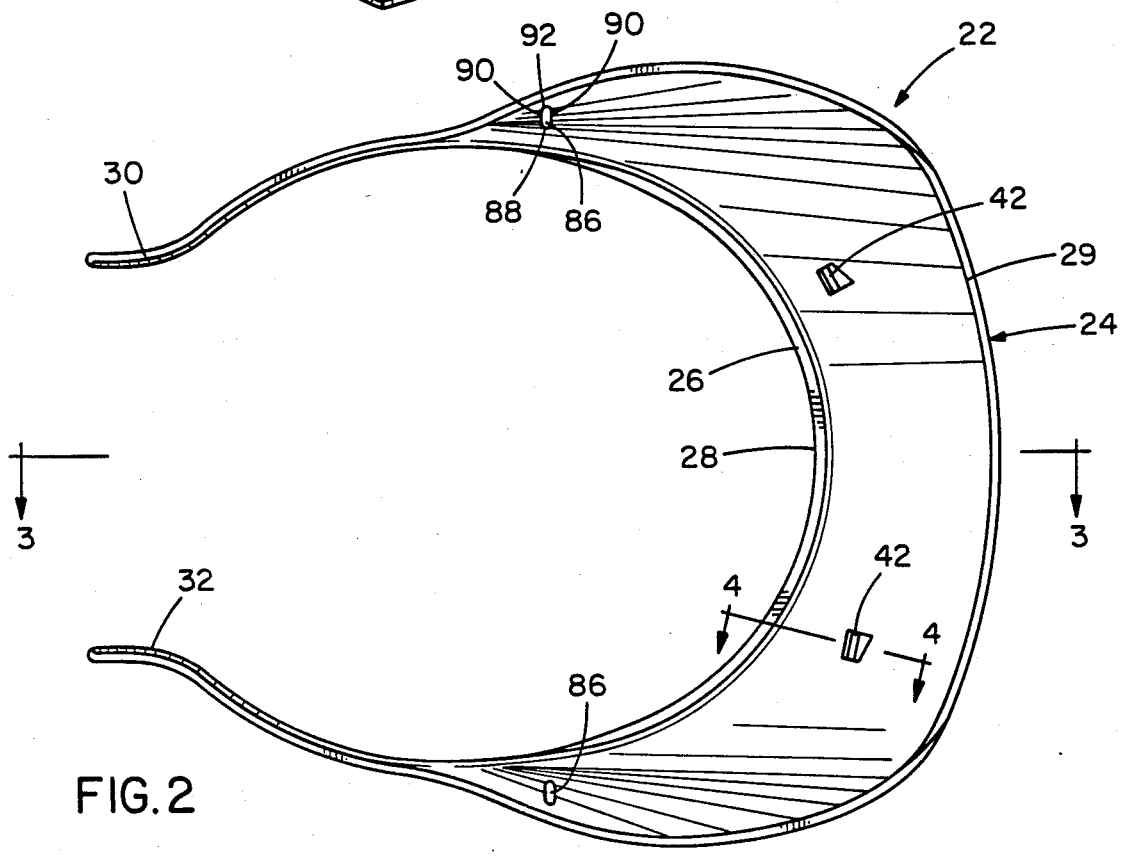
FIG. 2 is a bottom view of the visor of FIG. 1.
Figure 3:
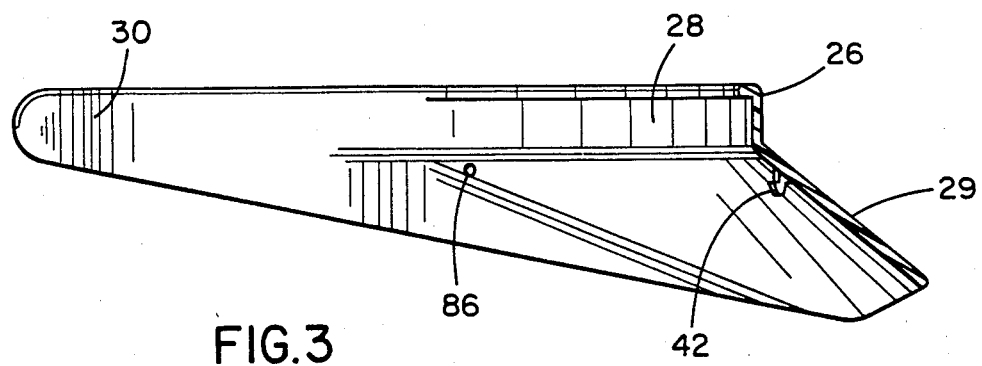
FIG. 3 is a sectional view taken generally along line 3—3 of FIG. 1.

More specifically, the visor 22 is a one-piece molded plastic construction made of a resilient material. Among preferred inexpensive thermoplastics are polystyrene and polyethylene. The legs 30 and 32, along with the brim 24 form a spring system allowing resilient deflection of the legs from an as-molded condition, as best shown in FIG. 2, in which the spacing between the legs is less than a corresponding dimension of the cranium, to an extended condition wherein the spacing between the legs is sufficient to receive the cranium therebetween. The spring system biases the legs toward their as-molded condition so that the engagement of the cranium by the legs, along with the engagement of the forehead by the brim inner surface 28, cooperate to cause the head to support the protective eyewear without the ears or nose carrying any significant weight which could cause discomfort to the wearer.

Because the posts 42 are the only connection between the bill 29 and the shield, and because these posts are located well inwardly of the ends 36, 38 of the shield, the connection of the shield to the bill does not cause any undue stiffening of the spring system making the protective eyewear 20 difficult to put on. Thus as the legs 30, 32 are spread toward their extended position, there is relative movement between the shield ends and adjacent portions of the bill.

The provision of the spaced mounted posts, as opposed to a single central post, offers greater stability and reduces twisting forces applied to the post in the event an end of the shield is struck. Also because the posts and sockets are disposed inwardly of the shield end, localized stress concentrations which are imposed on these connection components during extension of the legs, are lowered. Particularly in cold weather when the plastics are more rigid, abruptly spreading the legs could impose such high localized stress concentrations on connections if they were located at the ends of the shield that the components could fracture.

The shield 34, which is also of one-piece construction with acrylate being a preferred material, is symmetrical about a vertical plane P as shown in FIG. 5 with each socket 44 located about midway between the plane and one of the ends 36 or 38. One method of formation of the shield is by molding. As shown in FIGS. 5 and 6, the shield includes a lens or arcuate viewing wall 46 for overlaying the eyes and which extends between the shield ends. A peripheral wall 48 is joined to the lens at each end and extends rearwardly therefrom. This configuration of lens and peripheral walls results in sufficient space in front of the eyes for prescription eyeglasses. The lens has a recess 50 for receiving the nose.

Details of construction of the posts 42 and the sockets 44 are best described with reference to FIGS. 4 and 7, respectively. Each socket 44 includes a front wall 52, a rear wall 54 and a pair of side walls 56 which define an aperture 58 for receiving a post 42. The front wall 52 is, in essence, a continuation of the viewing wall or lens 46. The rear wall 54 of the socket includes a nose 60 extending into the aperture 58 to divide it into an entrance portion 62 and a constricted throat portion 64. The inner surface 66 of the front wall 52 cooperates with a follower surface 68 on the post to guide the post into the socket.

Front wall 52 is provided with an abutment surface 70 while the bill 29 as an engagement surface 72 at the basal end of the post. These last-mentioned surfaces cooperate to limit insertion of the post into the socket.

Each post 42 also has a barb 74 for cooperating with the nose 60 of the socket rear wall 54 so that once the post is fully inserted into the socket, it can be extracted only with difficulty. More specifically, the barb includes an angled deflection surface 76 for engaging an entry surface 78 of the nose so that advancement of the post into the socket results in mutual deformation of the nose and barb until the barb moves beneath the level of the nose. Finally, the nose 0 has a locking surface 80 for cooperating with an undercut surface 82 of the barb to maintain the post fully inserted in the socket.

The shield 34 is mounted on the bill 29 of the visor 22 as follows. After the shield is held so that the sockets are aligned with their corresponding posts, the bill and the shield are simply pushed together causing the posts 42 to enter their corresponding sockets 44. The deflection surface 76 of the barb and the entry surface 78 of the nose function to cam the components so that they are mutually deformed thereby allowing the barb 74 to move beneath the level of the nose 60. Of course, the locking surface 80 cooperates with the undercut surface 82 of the barb to prevent withdrawal of the post from the socket without a great deal of difficulty. Thus, the shield 34 is held firmly to the bill of the visor.

Each peripheral wall 48 of the lens 46 is preferably provided with an upwardly extending peg 84 which is received in one of a pair of elongated apertures 86 at the sides of the bill 29. The apertures extend laterally, in the direction the legs 30, 32 move when deflected outwardly to permit mounting of the protective eyewear 20. Each aperture 86 is defined by an inner abutment surface 88. When the legs 30, 32 are in their undeflected positions, the pegs 84 are spaced from the corresponding abutment surfaces 88. Thus during deflection of the legs to mount the eyewear, the apertures 86 move outwardly with respect to the pegs 84 so that the pegs on the shield 34 do not operate as would a solid connection between the shield 34 and bill 29 at the ends of bill, to substantially stiffen the visor.

However, when the legs 30, 32 are spread, engaging the head of the wearer, the pegs are positioned closely adjacent the abutment surfaces 88. Thus, upon application of an inwardly directed force to one of the peripheral walls 48, the peg 84 of that peripheral wall engages its corresponding inner abutment surface 88 to resist inward movement of the peripheral wall. Unrestrained movement of the peripheral wall in response to such a force could result in fracture of the shield 34.

Each of the apertures 86 is further defined by spaced side abutment surfaces 90 and an outer abutment surface 92. An abutment surface 90 is engaged by a peg 84 to limit movement of the shield in response to a blow applied to the front of the lens 46 adjacent one of the peripheral walls 48. A blow from near the center of the lens would tend to drive the peripheral walls outwardly, pivoting about the posts 42. However, the engagement of the pegs 84 with the outer abutment surfaces 92 limits such movement.

An alternative embodiment of the shield 34 of the present invention is best shown by reference character 34A in FIG. 8. Components of shield 34A corresponding to components of shield 34 are designated by the reference numeral assigned to the components of shield 34 with the suffix "A". The main difference between shield 34A and shield 34 is that the peripheral walls 48A and the lens 46A are integrated and, in essence, together form a portion of the surface of a cone. The viewing shield 34A provides a somewhat closer fit to the eyes than does shield 34 and is intended for use by a person who does not wear prescription glasses.

It will be appreciated that the protective eyewear 20 of the present invention offers several advantages over either safety glasses or full hard hats having transparent shields. The protective apparatus 20 is relatively inexpensive as it is formed by two molded plastic components which fit together easily. The apparatus leaves the top of the head uncovered to promote better ventilation and the protective apparatus can be simply donned by separating the legs 30 and 32 and moving the visor rearwardly until the inner surface 28 of the brim 24 engages the forehead. As the protective apparatus is inexpensive, it is more likely that it would be provided for visitors at a factory or a construction site. Because the protective apparatus 20 is easy to don, is lightweight and is comfortable to wear, it is more likely that the visitor will use the protective apparatus thereby promoting increased safety.

The inner surface 28 of the visor 22 may be lined with a sweatband. Also an elastic band can be provided attached to the free ends of the legs 30, 32 to permit the eyewear 20 to hang from the neck of the user when not worn on the head.

In view of the above, it will be seen that the several objects of the invention are achieved and other advantageous results attained.

As various changes could be made without departing from the scope of the invention, it is intended that all matter contained in the above description or shown in the accompanying drawings shall be interpreted as illustrative and not in a limiting sense.

What is claimed is:

1. Protective apparatus for shielding the eyes of the wearer, said apparatus comprising:
   a one-piece molded plastic visor formed of resilient material and including a brim having an inner surface for engaging the forehead and a bill extending outwardly, said visor further including first and second spacings extending rearwardly from the brim for compressively engaging the head therebetween, said legs and said brim forming a spring system allowing a resilient deflection of said legs;
   a transparent shield dependent from said bill for overlaying the eyes, said shield having a first end disposed adjacent said first leg, a second end disposed adjacent said second leg and an upper surface extending intermediate said ends and positioned closely adjacent said bill; and
   means fixedly connecting said shield to said brim, said fixedly connecting means having socket means carried by one of said bill and visor and further comprising bayonet means for reception by said socket means and carried by the other of said bill and visor said fixedly connecting means being disposed spaced inwardly of said shield ends to permit relative movement between said shield ends and adjacent portions of said bill when said legs are deflected to permit mounting of said apparatus on the head whereby the presence of said shield does not substantially stiffen said spring system of said visor, wherein said socket means comprises a socket having an enlarged entrance portion leading to a constricted throat portion, and wherein said bayonet means comprises a tapered post having an enlarged head for reception in said socket in an interference fit.

2. Protective apparatus as set forth in claim 1 wherein said shield comprises said socket and further includes a viewing wall extending between said ends, said wall partially defining said socket entrance portion and said constricted throat portion.

3. Protective apparatus as set forth in claim 2 wherein said viewing wall includes a guide surface and said post includes a following surface, the last-mentioned surfaces cooperating to guide said post into said socket.

4. Protective apparatus as set forth in claim 1 wherein said socket has an abutment surface and said bill has an engagement surface, the last-mentioned surfaces cooperating to limit the extent of insertion of said post into said socket.

5. Protective apparatus as set forth in claim 1 wherein said socket includes a nose extending into the opening of said socket to define said constricted throat portion, and wherein said post includes a barb for cooperating with said nose to prevent the post, once fully inserted in said socket, from extraction from said socket without difficulty.

6. Protective apparatus for shielding the eyes of the wearer, said apparatus comprising:
   a one-piece molded plastic visor formed of resilient material including a brim having an inner surface for engaging the forehead and a bill extending outwardly, said visor further including first and second spaced legs extending rearwardly from the brim for compressively holding the head therebetween, said legs and said brim forming a spring system allowing resilient deflection of said legs from an as-formed condition to an extended condition to permit mounting of the visor by moving it rearwardly until the brim inner surface engages the forehead;
   a one-piece transparent shield formed of plastic material dependent from the brim for overlaying the eyes, said shield having a first end disposed adjacent said first leg, second end disposed adjacent the second leg and an upper surface extending intermediate said ends and positioned closely adjacent said bill; and
   a pair of spaced posts extending from one of said bill and said shield and received in a pair of corresponding sockets in the other of said bill and shield, said posts fixedly connecting said shield to said bill, said posts being the sole connection between said bill and said shield and said posts being disposed remote from said ends whereby the connection of said shield to said bill does not result in substantial stiffening of said spring system so as to unduly interfere with the ease with which said legs can be deflected, wherein the posts are carried by the bill, each post having a barb and each socket having an aperture for receiving one of the posts, each socket further including a nose extending into said aperture and cooperating with said barb to lock a post, once fully inserted, in the socket.

7. Protective apparatus for shielding the eyes of the wearer, said apparatus comprising:
   a one-piece molded plastic visor formed of resilient material including a brim having an inner surface for engaging the forehead and a bill extending outwardly said visor further including first and second spaced legs extending rearwardly from the brim for compressively holding the head therebetween, said legs and said brim forming a spring system allowing resilient deflection of said legs from an as-formed condition to an extended condition to permit mounting of the visor by moving it rearwardly until the brim inner surface engages the forehead;

a one-piece transparent shield formed of plastic material dependent from the brim for overlaying the eyes, said shield having a first end disposed adjacent said first leg, a second end disposed adjacent the second leg and an upper surface extending intermediate said ends and positioned closely adjacent said bill; and a pair of spaced posts extending from one of said bill and said shield and received in a pair of corresponding sockets in the other of said bill and shield, said posts fixedly connecting said shield to said bill, said posts being the sole connection between said bill and said shield and said posts being disposed remote from said ends whereby the connection of said shield to said bill does not result in substantial stiffening of said spring system so as to unduly interfere with the ease with which said legs can be deflected, wherein said shield includes a generally upwardly extending peg adjacent each of said ends, said bill having a pair of elongated apertures receiving said pegs, said apertures extending laterally in the general direction the legs move when deflected, each aperture being defined by an inner abutment surface, each peg being spaced from its corresponding abutment surface when said legs are not deflected.

* * * * *

UNITED STATES PATENT AND TRADEMARK OFFICE
CERTIFICATE OF CORRECTION

PATENT NO. : 4,815,838
DATED : March 28, 1989
INVENTOR(S) : John R. Liautaud

It is certified that error appears in the above-identified patent and that said Letters Patent is hereby corrected as shown below:

Column 1, line 32, change "4,541.125" to --4,541,125--.
Column 4, line 4, change "as" to --has--.
Column 4, line 15, change "0" to --60--.
Column 5, line 46, change "spacings" to --spaced legs--.
Column 6, line 44, after "leg" insert --a--.

Signed and Sealed this

Tenth Day of October, 1989

Attest:

DONALD J. QUIGG

*Attesting Officer*  *Commissioner of Patents and Trademarks*